(12) United States Patent
Wenstrand

(10) Patent No.: US 7,091,867 B2
(45) Date of Patent: Aug. 15, 2006

(54) WAVELENGTH SELECTIVITY ENABLING SUBJECT MONITORING OUTSIDE THE SUBJECT'S FIELD OF VIEW

(75) Inventor: John S. Wenstrand, Menlo Park, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 149 days.

(21) Appl. No.: 10/783,179

(22) Filed: Feb. 20, 2004

(65) Prior Publication Data

US 2005/0185243 A1 Aug. 25, 2005

(51) Int. Cl.
*G08B 23/00* (2006.01)

(52) U.S. Cl. .................. 340/576; 359/229; 359/548; 340/439

(58) Field of Classification Search ................ 340/576
See application file for complete search history.

(56) References Cited

U.S. PATENT DOCUMENTS

| | | | |
|---|---|---|---|
| 4,028,725 A | 6/1977 | Lewis | |
| 4,513,317 A | 4/1985 | Ruoff, Jr. | |
| 6,456,262 B1 | 9/2002 | Bell | |
| 6,856,873 B1* | 2/2005 | Breed et al. | 701/45 |
| 6,873,714 B1* | 3/2005 | Witt et al. | 382/118 |
| 6,926,429 B1* | 8/2005 | Barlow et al. | 340/576 |
| 2004/0070509 A1* | 4/2004 | Grace et al. | 340/576 |
| 2005/0007552 A1* | 1/2005 | Fergason et al. | 351/210 |

* cited by examiner

*Primary Examiner*—Daniel Wu
*Assistant Examiner*—Eric M. Blount

(57) ABSTRACT

A detection system for monitoring a subject remains outside the normal field of view of the subject by using a wavelength selective optical member. In one application, an eye of a driver is repeatedly or continuously illuminated and imaged without effect on the field of view of the driver. A dichroic mirror may be used to provide the wavelength selectivity. For the application in which the system is used for a motor vehicle, such as an automobile, the dichroic mirror may be achieved by coating a portion or all of the windshield so as to pass visible light, while reflecting detection light. Other applications of the detection system include monitoring a subject engaged in a person-to-person interaction, wherein a dichroic mirror is defined by a divider between the two persons.

24 Claims, 4 Drawing Sheets

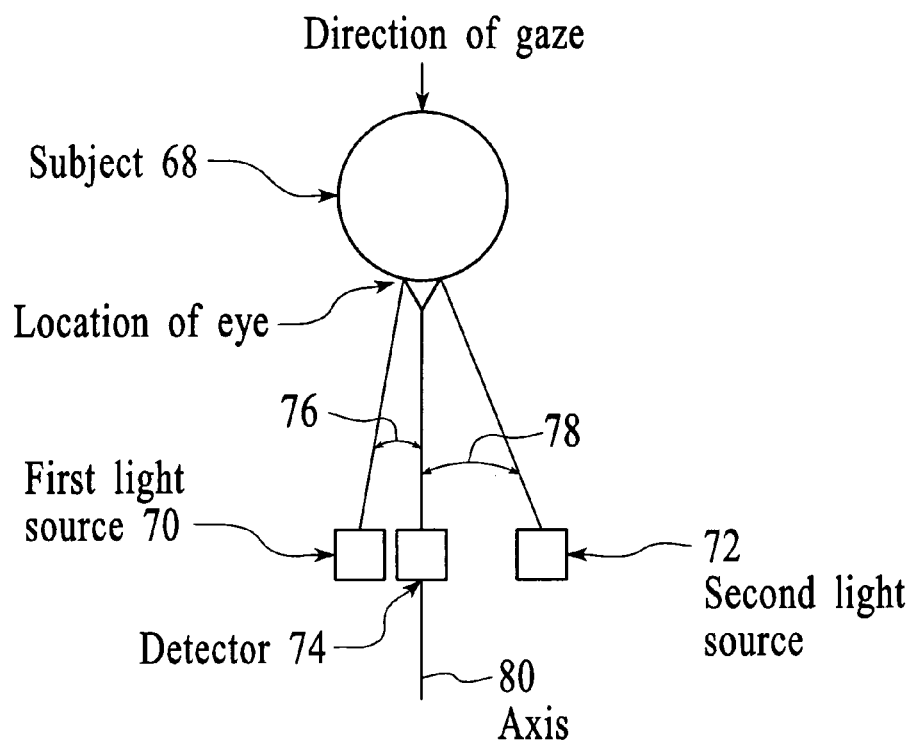
FIG. 6
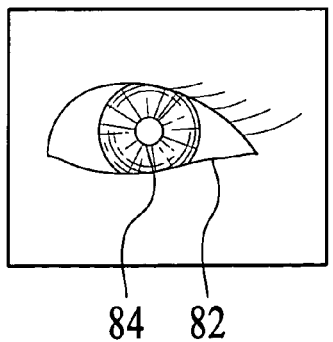
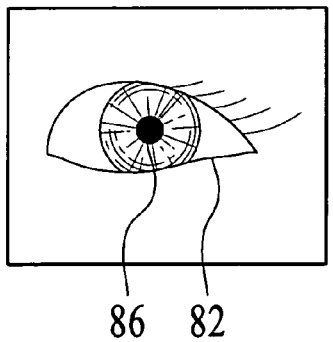
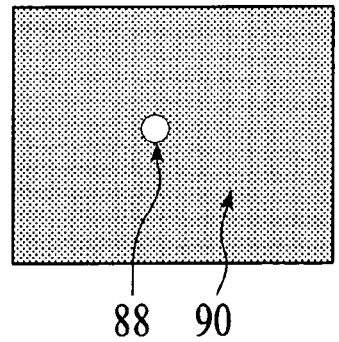
FIG. 7  FIG. 8  FIG. 9

WAVELENGTH SELECTIVITY ENABLING SUBJECT MONITORING OUTSIDE THE SUBJECT'S FIELD OF VIEW

BACKGROUND ART

In a variety of different applications, it is of interest to acquire information regarding an individual without diverting the attention of the person. In one such application, a system may be used to monitor the perceived drowsiness of a driver of a motor vehicle, such as an automobile, train, airplane and the like. There are also security applications, such as the verification of the identity of a driver or the identity of a patron of a business (e.g., a bank). One technique for monitoring drowsiness, verifying identity, or determining other individual-specific information is to acquire data directly relating to the eyes of a person. Images of a person's pupil may be used in the same manner as a fingerprint. The degree or the length of time that the eyes of a person are open or closed may be used as an indication of a level of drowsiness of the person.

Concerns with known approaches to acquiring the data include minimizing the distraction to the individual and minimizing the obstruction of the view of the individual, while maintaining the reliability of the acquired data. In monitoring the eyes of a motor vehicle driver, light may be reflected off the eyes of the person and then detected by a camera. A low profile system having an illumination source and a suitable camera may be used, but the system will nevertheless reduce the field of view of the driver.

The reliability of the acquired data is dependent upon the ability of the system to distinguish the features of a person. Light received by a detector (such as a camera) following reflection from the targeted person must be distinguishable from the light received following the reflection from another person or from a structure, as well as light received directly from another source, such as the sun or headlights of another car.

SUMMARY OF THE INVENTION

A detection system for acquiring information regarding a subject (person) utilizes wavelength selectivity to enable monitoring of the subject at a location or locations outside the normal field of view of the subject. The subject is typically a "viewer," in the sense that this field of view is significant to the subject. As examples, the subject may be a driver of a motor vehicle or may be an individual engaged in an interview.

The wavelength selectivity is provided by an optical member that is positioned between an intended location of the "viewer" and the environment of interest to the viewer. In a motor vehicle application, the optical member is the windshield of the vehicle, while in other applications the optical member may be a specifically designed divider. At least a portion of the optical member is wavelength-selective with respect to reflectivity characteristics. Specifically, the optical member is generally transmissive with respect to visible light, but is substantially reflective with respect to a particular detection wavelength or range of wavelengths. As one possibility, the detection wavelength may be that of infrared (IR) light. The optical member is positioned so as to reflect the light within the detection wavelength range to a detector which is positioned outside the normal field of view of the viewer.

For systems that include the source or sources of the light having the detection wavelength, each source is also located outside of the normal field of view of the viewer. A pair of IR emitters may be positioned beyond the boundary of the optical member and may be directed to reflect light off the optical member to the face of the viewer. Back-reflected light from the viewer is redirected by the optical member to the location of the detector.

For a system specifically designed for a motor vehicle, the windshield may include conventional coatings for achieving desired optical properties, but at least a portion of the windshield includes a coating which defines a dichroic mirror which is generally transparent to visible light and substantially reflective with respect to a driver-detection range of wavelengths. A detector is positioned to receive reflected light within the range of wavelengths following reflection from the windshield. The detector is positioned outside any line of sight from the driver to the windshield. The output of the detector is coupled to a processor for determining information regarding the driver. The system may be dedicated to monitoring the alertness of the driver, may be dedicated to verifying the identity of the driver, or may serve a number of purposes. The detector may be embedded within the dashboard of the motor vehicle in order to completely eliminate any possibility of obstructing the view of a driver. Similarly, any light sources that are a part of the system may be embedded within the dashboard or may be located in other positions that do not affect the field of view. In the applications involving driver monitoring, the optical member has a unitary magnification and the view of the driver is not affected by the output of the driver (i.e., the driver's vision remains independent of the detector output). The invention may be used in an automobile, airplane or other vehicle that is driven by means of a motor.

In other applications, the optical member may merely be a divider between two persons engaged in a business transaction. As one possibility, the divider may be a glass member used at a station of a bank.

BRIEF DESCRIPTION OF THE DRAWINGS

FIG. 6 is a conceptual view of using a pair of light sources for pupil detection in accordance with the invention.

FIGS. 7, 8 and 9 are images of a human eye captured by the system of FIG. 6.

DETAILED DESCRIPTION

Figure 1:
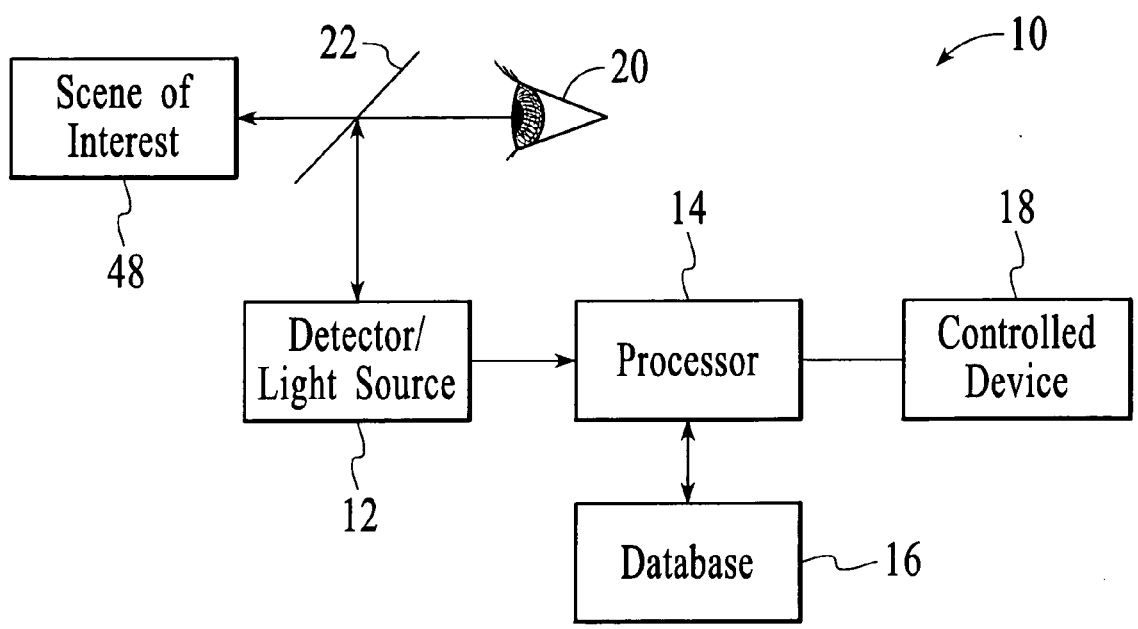
FIG. 1 is a block diagram of components of a system for monitoring a subject in accordance with the invention.

With reference to FIG. 1, a system 10 that utilizes wavelength selectivity to enable a subject to be monitored without obstructing the field of view of the subject is shown as including a detector/light source 12, a processor 14, a database 16, and a controlled device 18. In the embodiment of FIG. 1, it is the eye 20 of the subject that is detected for the purpose of acquiring information regarding the subject and it is an optical member 22 that provides the desired wavelength selectivity. The optical member is a dichroic mirror that is generally transmissive with respect to visible light and substantially reflective with respect to a particular detection wavelength, such as infrared (IR) light. By "substantially reflective," what is meant herein is that the detection wavelength is sufficiently reflected by the dichroic mirror to allow the detector to acquire reliable information regarding the subject. Thus, less than 100% of the energy at the detection wavelength need be reflected by the dichroic mirror. Similarly, less than all of the light within the visible light spectrum may pass through the dichroic mirror without affecting the optical member's characterization as being "generally transmissive." For example, windshields of automobiles often have coatings designed to shield the passengers of the automobile from certain thermal or optical effects of the sun. Such coated windshields will have a transmissivity within the visible light range ($T_{vis}$) that is below 100%, but the windshields are generally transmissive. A $T_{vis}$ value of at least 70% is desired for automobile windshields.

Figure 2:
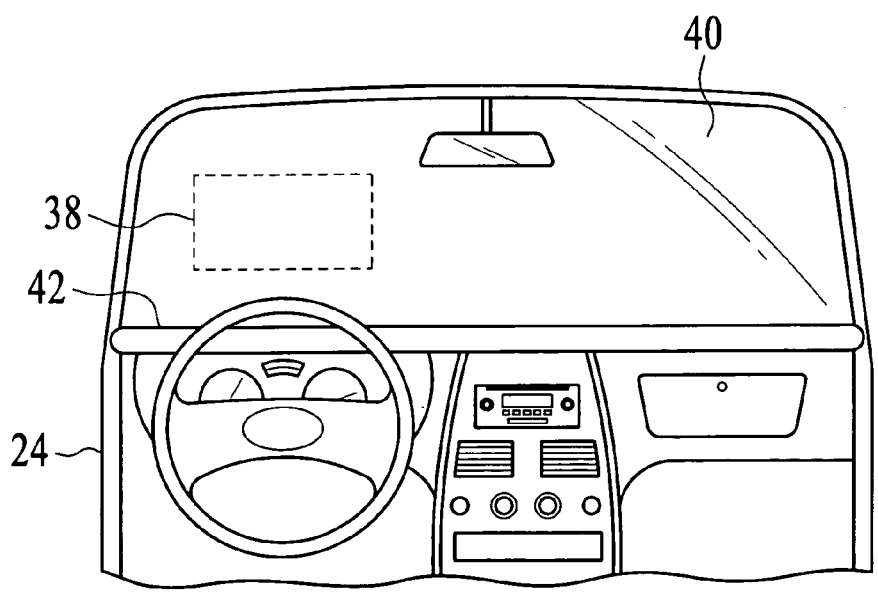
FIG. 2 is a front view of the interior of an automobile which has been equipped with a subject monitoring system in accordance with the invention.
Figure 3:
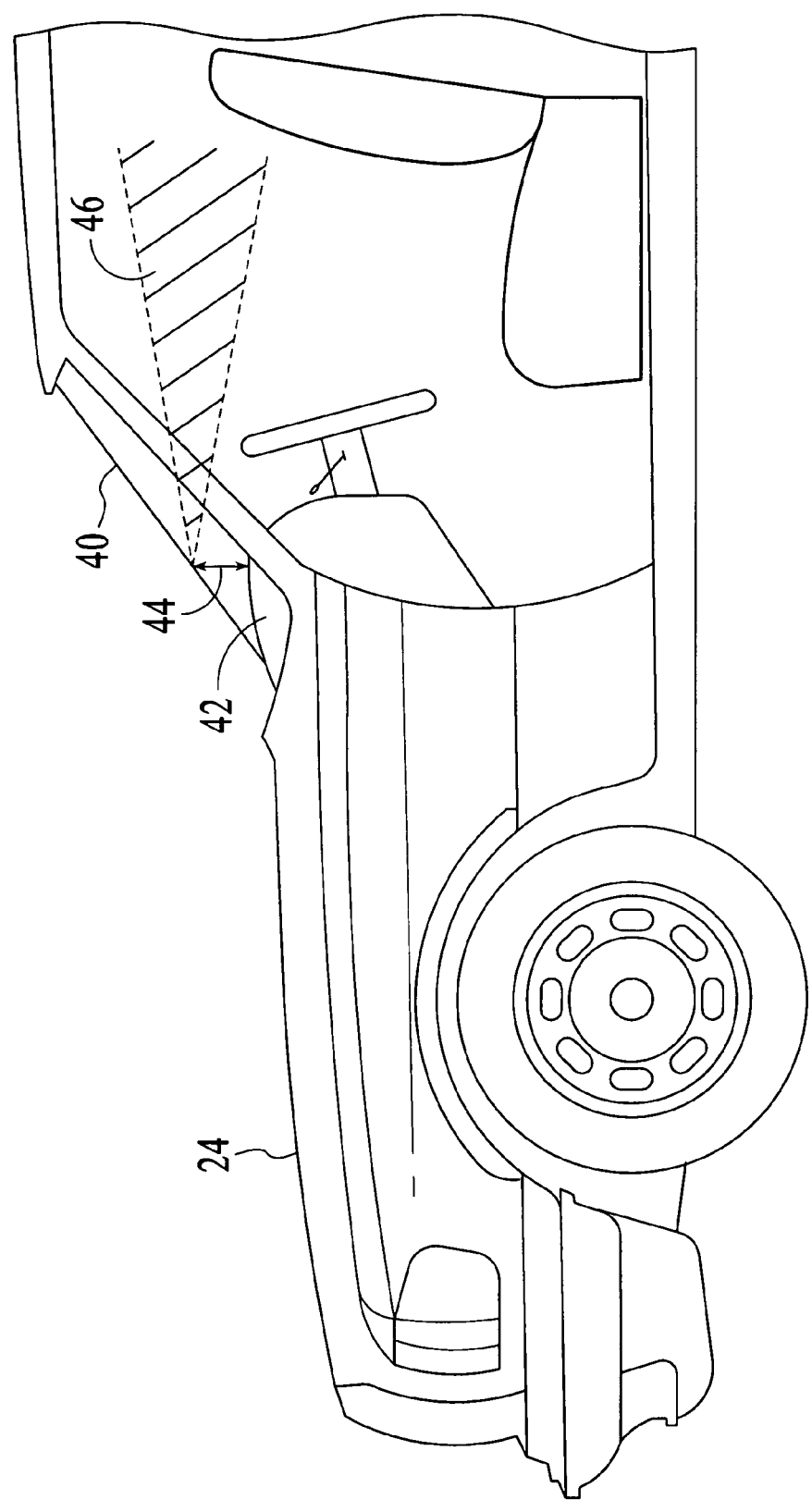
FIG. 3 is a side view of the automobile of FIG. 2.
Figure 4:
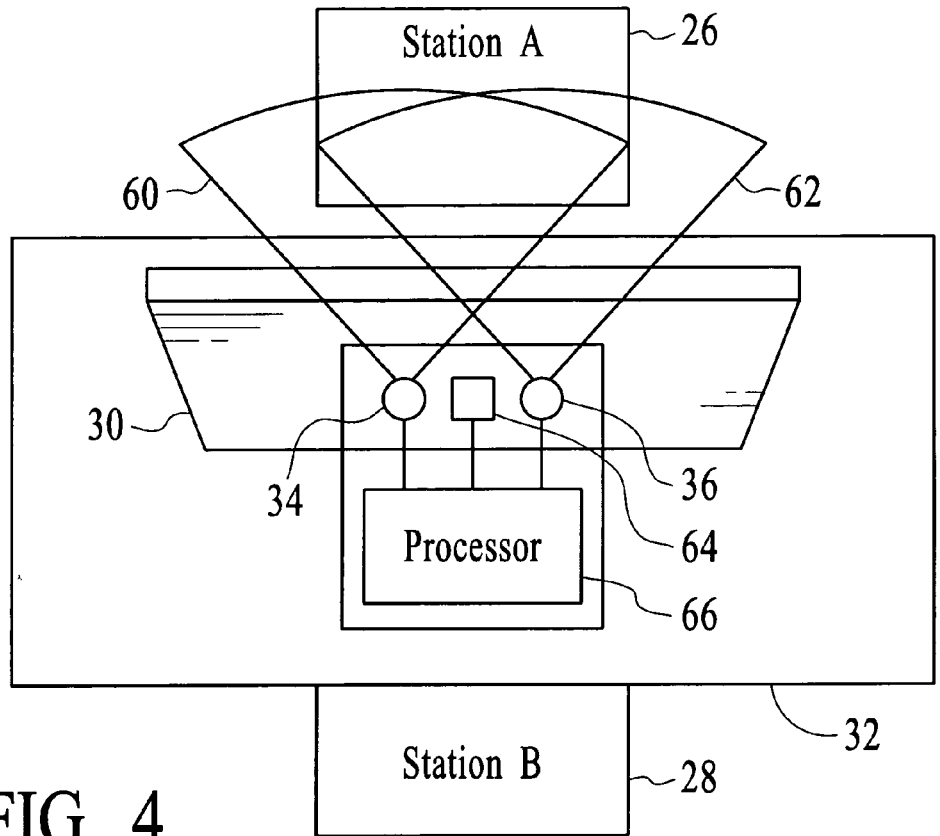
FIG. 4 is a top view of the application of the system of FIG. 1 in an environment involving person-to-person interaction.

FIGS. 2, 3 and 4 illustrate two applications of the system 10 of FIG. 1. In FIGS. 2 and 3, the system is incorporated into an automobile 24. The system is equally applicable to other vehicles, whether designed to travel on rails (e.g., trains or mass transit vehicles of a metropolitan area) or designed to travel by air (e.g., airplanes or helicopters). In FIG. 4, the system is incorporated into an environment involving person-to-person interaction, such as at a bank window or location for conducting an interview. As will be explained more fully below, the "subject" is located at Station A 26 and is separated from a second person at Station B 28 by a divider 30 angled non-perpendicularly upward from a desk 32. The divider forms a dichroic mirror, with the angle of the divider being such that light from sources 34 and 36 is directed upwardly and reflected by the divider to the person at Station A.

Referring to FIGS. 1 and 2, dashed lines 38 on the windshield 40 of the car 24 represent the portion of the windshield that is coated in order to form a dichroic mirror that is aligned with the detector/light source 12 of the system 10. In most applications, the entire windshield is coated, but there may be some applications in which it is advantageous to selectively coat one or more regions of the windshield. While not shown in FIG. 2, the detector/light source may be embedded within the dashboard 42 of the automobile. Consequently, the system does not obstruct the field of view of the driver. Persons of ordinary skill in the art are aware of coatings for providing the desired wavelength selectivity.

In FIG. 3, double-arrowed line 44 represents IR light or other light having the detection wavelength being directed to and received from the properly coated portion of the windshield 40. For applications in which the light source or light sources are located remotely from the detector or are not used, only the downwardly directed arrow is relevant. The shaded area 46 represents the "cone of vision" with respect to monitoring a driver of the vehicle. The system may be used to detect the eyes of the driver for the purpose of determining whether the driver is drowsy. Thus, the controlled device 18 of FIG. 1 may be an alerting device that is triggered when information regarding the eyes of the driver indicates that a level of drowsiness has been exceeded. Alternatively, the system 10 may be used for security reasons to verify the identity of the driver. In this application, the database 16 may be a database of acceptable drivers. In this security situation, the controlled device 18 may be designed to disable the car as a response to the inability to verify the identity of the driver.

In the embodiment of FIGS. 2 and 3, the "optical member" of the system (i.e., the windshield 40) has a unitary magnification. As a result, the "scene of interest" 48 in FIG. 1 is viewed without magnification or demagnification. This is distinguishable from the use of an eye detection system in viewing a miniaturized display or the like. Moreover, it should b noted that the controlled device 18 does not affect the optical properties along the visible light path from the subject to the scene of interest to the driver. That is, regardless of the output of the processor 14, the objects in the environment in front of the automobile 24 will appear the same to a driver with open eyes.

Figure 5:
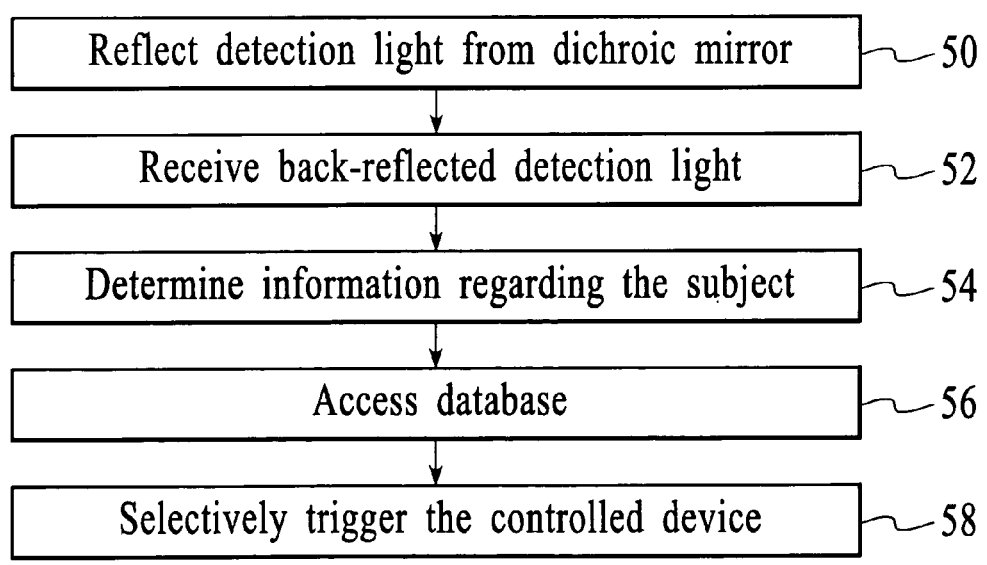
FIG. 5 is a process flow of steps of one implementation for utilizing the system of FIG. 1.

In operation, the light having the detection wavelength (e.g., IR light) may be directed upwardly from the dashboard 42 of the automobile 24, because the windshield 40 is partially or entirely coated to reflect the detected light, while passing visible light. In FIG. 5, the process is shown as including the step 50 of reflecting detection light from the dichroic mirror. However, there may be some applications in which the targeted feature for detection (e.g., the eyes of the driver) reflects or generates sufficient light of the detection frequency without the need of a light source that is dedicated to the system 10.

At step 52, the back-reflected detection light is received. Thus, IR light from a driver's eye 20 of FIG. 1 is reflected by the optical member 22 to the detector/light source 12. In FIG. 2, the detector is positioned to receive reflected light from the coated portion 38 of the windshield 40, but without obstructing vision through the windshield. As one possibility, the detector is a charge-coupled device (CCD) imager. Alternatively, the detector may be a complementary metal-oxide semiconductor (CMOS) imager. In general, CMOS imagers are less expensive than CCD imagers and sometimes provide better sensitivity at infrared/near-infrared wavelengths than CCD imagers. However, the invention is not limited with respect to the type of imager.

Information regarding the subject may then be determined, as indicated at step 54. Frames of information may be generated by the detector and then manipulated by the processor 14 of the system 10. As previously mentioned, the information may relate to the level of drowsiness or attentiveness of a driver. Alternatively, the system may be dedicated to determining the line of sight of the driver. As another possibility, the system may be security based, such as providing verification of the identity of the driver. Retinal detection and iris detection may be used as a basis for distinguishing a person, in the same manner as the use of a fingerprint. A database 16 of "allowed drivers" may be accessed by the processor 14 of the system 10, as one possibility of the execution of the step 56 in FIG. 5.

In step 58, the controlled device 18 of FIG. 1 is triggered, when appropriate. For example, when the drowsiness or attentiveness of the driver is the concern, an alerting device may be triggered when it is determined that a threshold level has been reached. Additionally, alternatively, the controlled device may be one which selectively enables or disables the automobile on the basis of a determination of the identification of the driver.

The steps of FIG. 5 may also be used in the application illustrated in FIG. 4. In this application, each light source 34 and 36 generates detection light that may be manipulated by one or more lenses to achieve a desired zone of view 60 and 62 after reflection by the appropriately angled divider 30 that exhibits dichroic properties. The light will illuminate features of a person located at Station A 26. Back-reflected light is redirected by the divider 30 to a detector 64. The detector is connected to a processor 66 for determining information regarding the person at Station A. Merely for the purpose of example, the identity of the person may be of interest for security reasons.

It has been determined that more reliable information regarding the face of a subject may be acquired by taking two images of the subject or the particular feature or features (eyes) of the subject. In this embodiment of high reliability, one of the images is acquired using lighting that is close to or directly on the axis of the detector ("on-axis imaging"), while the other image is acquired using lighting that is at a greater angle to the detector ("off-axis imaging"). When the eyes of a subject are open, the difference between the two images will highlight the pupils of the eyes, because the somewhat diffuse reflection from the retinas is detected only in the on-axis image. The strong pupil signal in the on-axis imaging is referred to as "red-eye" in conventional flash photography. Other facial and environmental features are largely cancelled, leaving the pupils as the dominant feature in a differential image. When the pupils are not detectable in the differential image, it is inferred that the eyes of the subject are closed. The amount of time that the eyes are open or closed can be monitored against a threshold, for example. Should the threshold not be satisfied, an alarm or some other action can be taken to alert the subject. Other factors, such as the frequency of blinking, can also be used.

In the driver drowsiness application, the amount of light reflected off the retina is also a function of the degree to which the eyelids of the subject are closed. In fact, reflection may be undetectable when the eyes are drooping or the subject is squinting. These factors of eyelid drooping and subject squinting may be correlated to fatigue or sleepiness.

In FIG. 6, the operation of one possible embodiment of the double image acquisition is shown without including the optical member that exhibits dichroic properties. In the application of the principles of FIG. 6 to the present invention, the optical member is positioned between the subject 68 and the optical components of the system, which are shown as including a first light source 70, a second light source 72, and a detector 74.

For clarity of illustration, the first light source 70 and the second light source 72 are shown on opposite sides of the detector 74 in FIG. 6. However, it is appreciated that the two light sources may instead be on the same side of the detector. A key principle in obtaining differential reflectivity from the retina of an eye is the dependence of retinal reflectivity on the angle between the source and the detector. This angle may be referred to as the "illumination angle." The selection of a position of a light source relative to the detector is subject to additional considerations. To achieve successful differencing of the images resulting in spots corresponding to the reflecting retina, it is desirable for the remainder of the field of view to have sufficiently similar illumination profiles under the two different angles of illumination. In the application of FIGS. 2 and 3, this "remainder of the field of view" may include the face of the driver, the apparel of the driver, and the interior of the automobile 24. For example, it is undesirable for illumination from a single-side, on-axis light source to produce shadows that are significantly different than the shadows produced by a second off-axis light source.

In FIG. 6, the first light source 70 is situated at a first illumination angle 76 from the axis 80 of the detector 74, while the second light source 72 is situated at a second illumination angle 78. In general, a smaller first illumination angle will decrease the retinal return. As used herein, the "retinal return" refers to the intensity (i.e., the real photon count or the equivalent) that is reflected from the back of the eye and that is received at the detector. As one possibility, the first illumination angle 76 is in the range of approximately zero degrees to three degrees.

In general, the size of the second illumination angle 78 is chosen so that only low retinal return from the second light source 72 will be detected at detector 74. The iris surrounding the pupil tends to block this signal, so that pupil size should be considered under different lighting conditions when selecting the second illumination angle 78. This second angle is larger than the first illumination angle 76. However, the second angle should be only slightly larger than the first angle so that, with the exception of the pupil, an image captured using the second light source will be similar to an image captured using the first light source. Accordingly, in one embodiment, the second illumination angle is in the range of approximately three degrees to fifteen degrees.

The first and second light sources 70 and 72 may emit light at generally equal intensities. However, there may be applications in which it is desirable for the light sources to emit light at different intensities. More likely, there are applications in which the light sources are designed to emit light at different wavelengths, so that the original images for forming the differential image can be formed on the basis of the difference in wavelengths. The wavelengths and/or illumination intensities of light emitted from the light sources are selected so that the light will not distract the subject and so that the iris of the subject's eyes will not contract in response to the light. A desirable selection is the use of infrared or near-infrared light sources.

FIG. 7 illustrates an image of an open eye, where the image is generated using the on-axis light source 70. The on-axis illumination angle results in the image having a bright pupil 84, as a result of the strong retinal return.

FIG. 8 illustrates an image of the open eye 82, but with an off-axis illumination angle, so that there is a dark pupil 86. The images of FIGS. 7 and 8 may be generated simultaneously or may be formed in successive frames of image information from a single detector.

FIG. 9 illustrates a differential image resulting from the difference between the two sets of image data generated using the on-axis and off-axis light sources. By taking the difference between the images of FIGS. 7 and 8, a relatively bright spot 88 will remain against the relatively dark background 90 when the eye is open. There may be vestiges of other features of the eye remaining in the background 90 but, in general, the bright spot will stand out in comparison to the background. When the eye is closed or nearly closed during the acquisition of the image data for forming FIGS. 7 and 8, there will be no bright spot or the bright spot will be partially deleted in the differential image.

FIGS. 7, 8 and 9 target one eye of the subject. It should be appreciated that both eyes may be monitored. It should also be appreciated that a similar effect may be achieved if the images include other features of the subject and/or features of the subject's environment. These other features will largely cancel out in a similar manner to many of the features of the eye, so that only the bright spot 88 will remain within the differential image.

Light from the two light sources 70 and 72 may be emitted in pulses that are synchronized with the frame rate of the detector 74. For example, if the detector operates at a frame rate of thirty frames per second, the light is emitted at a rate of thirty pulses per second. However, it is not necessary that the pulsing occurs continuously. For example, if the frame rate is thirty frames per second, four pulses may be emitted for four/thirtieth of a second, with no light pulses being emitted over the remaining twenty-six/thirtieth of the second. It is possible for sufficient information to be collected during the small portion of the second, with a reduced likelihood of distracting the subject.

The light from the light sources 70 and 72 of FIG. 6 may or may not be of the same wavelength. In an embodiment in which light is emitted at essentially the same wavelength, the light sources may be activated at different times. That is, for example, a pulse may be emitted from the first light source 70, followed by a pulse from the second light source 72, and so on for the length of a burst. In general, it is desirable for the light sources to alternate emitting light pulses, so as to generate consecutive on-axis and off-axis frames of image information. For example, even-numbered frames may be associated with pulses of the first light source, while odd-numbered frames are associated with pulses of the second light source. Since the frame acquisition is rapid, the images will be very similar, reducing motion artifacts and thereby facilitating the process of finding the difference between any two consecutive frames.

As an alternative to forming a differential image on the basis of two consecutively acquired frames of information, the image frames may be simultaneously collected. This is possible if the image data collection is distinguished by optical property, such as wavelength or polarization. For example, if the light emitted from the first light source 70 of FIG. 6 is at a different wavelength from the light emitted from the second light source 72, the light may be emitted at essentially the same time. In one such embodiment, the wavelength that yields the strongest retinal return is used by the light source closest to the detector 74. Measured on a conventional silicon-based detector, the retinal return signal is typically stronger at wavelengths of 800 nanometers (nm) versus 950 nm. In general, it is more desirable to associate the shorter wavelength with the on-axis light source.

When the light is emitted from both light sources 70 and 72 at essentially the same time, the on-axis and off-axis frames will be acquired essentially simultaneously by the detector 74. As a result, motion artifacts can be eliminated and any timing constraints placed on the detector can be relaxed. Furthermore, the timing between consecutive measurement cycles can be less critical. This allows the time between consecutive measurement cycles to be increased without jeopardizing the reliability of the process. For example, images can be acquired once per second, rather than four times per second. The advantages that are realized by increasing the measurement cycle include increased sensitivity to the captured images, reduced image handling requirements, lower cost, and decreased exposure of the subject.

Using different wavelengths for the two light sources 70 and 72, the on-axis and off-axis frames can be acquired using various methods. Some of these methods include using bulk optics, while others use sensors with pixel-based filters.

Polarization is an alternative basis for separating the two signals. In one embodiment, the first light source 70 emits light that is polarized in one direction, while the second light source 72 emits light polarized in an orthogonal direction. Typically, two detectors are used, rather than the single detector 74 shown in FIG. 6. Appropriate polarizers can be positioned in front of the detectors or a polarizing beam splitter can be used.

Any of the various embodiments for collecting images of a person's eyes may be used to monitor the drowsiness (or conversely, the alertness) of the person, such as a driver of the automobile 24 of FIGS. 2 and 3. As one possibility, the amount of time that the eyes of the subject are open can be measured and compared against a predetermined threshold. Failure to satisfy the threshold would indicate that the eyes have been closed or nearly closed for a prolonged period, suggesting that the operator is falling asleep. In such a situation, an alerting device may be triggered. However, other approaches to inferring drowsiness may be employed.

What is claimed is:

1. A system for enabling automatic determinations of information regarding a person engaging in a business transaction comprising:

an optical member positioned between an intended location of a viewer and an environment of interest to said viewer, said viewer being said person engaging in said business transaction and said environment of interest including an anticipated location of a second person engaging in said business transaction, said optical member being a divider that is fixed in position relative to said environment of interest, wherein a visible light path from said viewer to objects in said environment has a substantially unitary magnification, at least a portion of said optical member being wavelength-selective with respect to reflectivity characteristics, such that said optical member is generally transmissive with respect to visible light and is substantially reflective with respect to a particular detection wavelength;

a detector for receiving light of said detection wavelength reflected by said optical member from said viewer within said intended location, said detector having a detector output that is responsive to said received light; and a processor connected to said detector for processing said detector output, wherein optical properties along said visible light path from said viewer to said objects remain independent of said processing, said processor being configured to identify information regarding said viewer.

2. The system of claim 1 wherein said processor is configured to correlate detection of human eyes to stored identifications of particular persons, thereby enabling said system to specifically identify said viewer based on said detection of eyes of said viewer.

3. The system of claim 1 further comprising a first light source for emitting first light having said detection wavelength, said first light source being directed to reflect said first light from said optical member to an anticipated position of eyes of said viewer within said intended location, said detector and said processor being dedicated to acquiring data that is specific to said eyes.

4. The system of claim 3 wherein said processor is configured to provide identification of said viewer, said processor having access to a database of alternative viewer identifications.

5. The system of claim 3 further comprising a second light source for emitting second light having said detection wavelength, said second light source being directed to reflect said second light from said optical member to said anticipated position of said eyes, but at an angle that is distinguishable from an angle of said first light, wherein said first light has a same wavelength as said second light and has a different polarization relative to said second light.

6. A system for eye detection comprising:

a dichroic mirror which is generally transparent to visible light and which reflects light having a specific wavelength range;

a first light source for emitting first light to impinge said dichroic mirror such that said first light is reflected at a first illumination angle;

a second light source for emitting second light to impinge said dichroic mirror such that said second light is reflected at a second illumination angle greater than said first illumination angle, said first light and said second light being equal with respect to wavelength and having substantially equal intensity within said specific wavelength range; and a detector located for receiving back-reflected light from said dichroic mirror as a consequence of reflection of said first and second light toward said dichroic mirror from a subject's eyes;

wherein said subject's eyes are detectable using the difference between back-reflected said first light and back-reflected said second light.

7. The system of claim 6 wherein said first and second light sources are sources of infrared (IR) light, said specific wavelength range reflected by said dichroic mirror including said IR light, said first and second light sources being synchronized to alternate with respect to emission, such that said detector alternates in generating image information as a consequence of receiving said back-reflected first light and generating image information as a consequence of receiving said back-reflected second light.

8. The system of claim 6 wherein said dichroic mirror is a divider between anticipated positions of said subject and a second person with whom said subject is interacting, said detector and said first and second light sources being located outside any line of sight from said subject to said divider, said detector being operatively associated with a processor to determine an identity of said subject.

9. The system of claim 6 wherein said dichroic mirror is a region of a windshield of a motor vehicle, said detector and said first and second light sources being embedded within a dashboard of said motor vehicle.

10. The system of claim 9 further comprising a processor for receiving data from said detector, said processor being configured to monitor pre-identified conditions indicative of drowsiness of a driver of said motor vehicle, said driver being said subject.

11. The system of claim 6 wherein said dichroic mirror is a limited region of a windshield of a motor vehicle, said detector and said first and second light sources being outside any line of sight from a driver to said windshield.

12. A system for a motor vehicle comprising:
a windshield with at least a portion having a coating which defines a dichroic mirror that is generally transparent to visible light and substantially reflective with respect to a driver-detection wavelength range;
a first pulsed light source for emitting timed pulses of first light toward said dichroic mirror, said first pulsed light source being positioned such that said first light is reflected toward an anticipated location of a face of a driver of said motor vehicle;
a second pulsed light source for emitting timed pulses of second light toward said dichroic mirror for reflection toward said anticipated location to illuminate said face at an angle greater than illumination by said first light, said first and second pulsed light sources being controlled to provide alternating emissions of said first and second light;
a detector for receiving reflected light within said driver-detection wavelength range following reflection from said windshield, said detector being controlled to form separate frames of back-reflected said first light and back-reflected said second light; and
a processor connected to said detector for determining information regarding said driver of said motor vehicle on a basis of differences between said frames of said back-reflected first light and said back-reflected second light.

13. The system of claim 12 wherein said detector is positioned outside any line of sight from said driver to said windshield.

14. The system of claim 13 wherein said detector is embedded in a dashboard of said motor vehicle.

15. The system of claim 12 wherein said first and second pulsed light sources and said detector are embedded in a dashboard of said motor vehicle.

16. The system of claim 15 wherein said first and second light sources are IR emitters.

17. The system of claim 12 wherein said processor is configured to monitor perceived conditions of drowsiness of said driver.

18. The system of claim 12 wherein said processor is configured to identify a specific said driver.

19. A method for use in a motorized vehicle comprising:
providing a windshield having a coating which defines a dichroic mirror that is generally transparent with respect to visible light and provides reflection of first light within a driver-detection range of wavelengths;
emitting timed pulses of first light from a first pulsed light source toward said dichroic mirror, said first pulsed light source being positioned such that said first light is reflected toward an anticipated location of a face of a driver of said motorized vehicle;
emitting timed pulses of second light from a second pulsed light source toward said dichroic mirror for reflection toward said anticipated location to illuminate said face at an angle greater than illumination by said first light, said first and second pulsed light sources being controlled to provide alternating emissions of said first and second light;
providing a detector in a position to receive reflected said first and second light from said windshield without obstructing vision through said windshield, including controlling said detector to form separate frames of back-reflected said first light and back-reflected said second light;
determining information regarding a driver of said motorized vehicle on a basis of differences between said frames of back-reflected first light and said back-reflected second light, including accessing data indicative of persons authorized to drive said motorized vehicle; and
selectively enabling said motorized vehicle on a basis of whether said driver is authorized.

20. The method of claim 19 further comprising directing at least one beam of said first light toward said windshield for reflection onto eyes of said driver, each said beam originating from a source that is located so as not to obstruct vision through said windshield.

21. The method of claim 20 wherein directing each said beam is implemented by embedding each said source in a dashboard of said motor vehicle.

22. The method of claim 20 wherein directing each said beam includes using an infrared light source.

23. The method of claim 19 wherein determining said information regarding said driver includes monitoring drowsiness.

24. The method of claim 19 wherein determining said information includes identifying said driver.

* * * * *